United States Patent
Obara et al.

(10) Patent No.: US 11,182,688 B2
(45) Date of Patent: Nov. 23, 2021

(54) PRODUCING A FORMULATION BASED ON PRIOR DISTRIBUTIONS OF A NUMBER OF INGREDIENTS USED IN THE FORMULATION

(71) Applicant: INTERNATIONAL BUSINESS MACHINES CORPORATION, Armonk, NY (US)

(72) Inventors: Yachiko Obara, Tokyo (JP); Tetsuro Morimura, Tokyo (JP); Hiroki Yanagisawa, Tokyo (JP)

(73) Assignee: International Business Machines Corporation, Armonk, NY (US)

(*) Notice: Subject to any disclaimer, the term of this patent is extended or adjusted under 35 U.S.C. 154(b) by 448 days.

(21) Appl. No.: 16/262,308

(22) Filed: Jan. 30, 2019

(65) Prior Publication Data
US 2020/0242498 A1 Jul. 30, 2020

(51) Int. Cl.
*G06N 7/00* (2006.01)
*G06N 20/00* (2019.01)
*G16C 20/30* (2019.01)

(52) U.S. Cl.
CPC .............. *G06N 7/005* (2013.01); *G06N 20/00* (2019.01); *G16C 20/30* (2019.02)

(58) Field of Classification Search
CPC .......... G06N 7/00; G06N 7/005; G06N 20/00; G16C 20/30
See application file for complete search history.

(56) References Cited

U.S. PATENT DOCUMENTS

| | | | | |
|---|---|---|---|---|
| 6,308,107 B1 * | 10/2001 | Conboy | ................. | G06Q 10/08 700/121 |
| 6,876,894 B1 * | 4/2005 | Chen | ................... | G06Q 30/0621 700/100 |
| 7,065,422 B1 * | 6/2006 | Green | ................ | G05B 23/0221 700/108 |
| 7,460,922 B1 * | 12/2008 | Singh | .................. | G03F 7/70491 438/40 |

(Continued)

FOREIGN PATENT DOCUMENTS

| | | |
|---|---|---|
| CN | 107077642 A | 8/2017 |
| DE | 112007001891 T5 * | 5/2009 ............. G01R 23/16 |

(Continued)

OTHER PUBLICATIONS

Andrieu, et al., An Introduction to MCMC for Machine Learning, Machine Learning, Jan. 2003, pp. 5-43, vol. 50, Issue 1-2, Kluwer Academic Publishers, The Netherlands.

(Continued)

*Primary Examiner* — Tung S Lau
(74) *Attorney, Agent, or Firm* — Tutunjian & Bitetto, P.C.; Randall Bluestone

(57) ABSTRACT

A computer-implemented method for producing a formulation based on a prior distribution of a number of ingredients used in the formulation includes grouping a set of energy functions based on a number of ingredients used in a formulation, generating a probability distribution using the set of energy functions, obtaining at least one sample of the formulation by sampling from the probability distribution based on a previous sample, and triggering fabrication of the formulation in accordance with the at least one sample.

20 Claims, 8 Drawing Sheets

(56) References Cited

U.S. PATENT DOCUMENTS

| | | | | |
|---|---|---|---|---|
| 8,012,764 | B2* | 9/2011 | Denny | H01J 49/0027 |
| | | | | 436/173 |
| 8,234,149 | B2* | 7/2012 | Spearman | G06Q 30/0202 |
| | | | | 705/7.31 |
| 8,744,185 | B2* | 6/2014 | Chang | G06T 7/11 |
| | | | | 382/173 |
| 9,218,567 | B2* | 12/2015 | Macready | G06N 10/00 |
| 9,728,667 | B1* | 8/2017 | Johnson | H01L 27/1446 |
| 10,048,668 | B2* | 8/2018 | Butcher | G06F 30/00 |
| 10,620,620 | B2* | 4/2020 | Moyne | G05B 23/0243 |
| 2006/0117077 | A1* | 6/2006 | Kiiveri | G16B 40/20 |
| | | | | 708/200 |
| 2008/0015721 | A1* | 1/2008 | Spearman | G06Q 10/087 |
| | | | | 700/99 |
| 2009/0281768 | A1* | 11/2009 | Fitzgerald | G06F 30/23 |
| | | | | 702/181 |
| 2014/0052285 | A1* | 2/2014 | Butcher | G05B 19/0426 |
| | | | | 700/98 |
| 2014/0187427 | A1* | 7/2014 | Macready | G06N 5/02 |
| | | | | 505/170 |
| 2016/0179577 | A1* | 6/2016 | Catthoor | G06F 9/505 |
| | | | | 718/104 |
| 2017/0139408 | A1* | 5/2017 | Moyne | G05B 23/0243 |
| 2017/0255592 | A1 | 9/2017 | Karimi et al. | |
| 2018/0342872 | A1* | 11/2018 | Mirzazad Barijough | |
| | | | | H02J 13/0017 |
| 2018/0365370 | A1* | 12/2018 | Egan | G06F 3/04815 |

FOREIGN PATENT DOCUMENTS

| | | | | |
|---|---|---|---|---|
| TW | 1308703 B | * | 4/2009 | G06F 17/00 |
| TW | 201510885 A | * | 3/2015 | G06Q 10/04 |

OTHER PUBLICATIONS

Jensen et al., Blocking Gibbs Sampling for Inference in Large and Complex Bayesian Networks With Applications in Genetics, May 1997, pp. 1-190, Aalborg University, Institute for Electronic Systems, Dept. of Computer Science, Denmark.

Bui-Thanh et al., FEM-Based Discretization-Invariant MCMC Methods for PDE-Constrained Bayesian Inverse Problems, Inverse Problems and Imaging, Oct. 2016, pp. 943-975, vol. 10 No. 4.

Bierkens et al., The Zig-Zag Process and Super-Efficient Sampling for Bayesian Analysis of Big Data, 2018, arXiv:1607.03188v2 [stat.CO] Apr. 23, 2018.

Hayashi, Kyoto University, Graduate School of Informatics, Department of Systems Science, Sakai Lab, Lecture notes describing Markov chain Monte Carlo (MCMC). Published prior to 2017.

* cited by examiner

PRODUCING A FORMULATION BASED ON PRIOR DISTRIBUTIONS OF A NUMBER OF INGREDIENTS USED IN THE FORMULATION

BACKGROUND

Technical Field

The present invention generally relates to artificial intelligence and machine learning, and more particularly to producing formulations based on prior distributions of a number of ingredients used in the formulations.

Description of the Related Art

Formulations, also referred to herein as compositions of ingredients, can be determined in a manner selected to satisfy one or more desired formulation properties or conditions. For example, in the case of fragrances, a fragrance formulation can have desired properties relating to aromatics (e.g., type of smell), popularity (e.g., frequent patterns of ingredient combinations and/or ingredient combinations that should be avoided), and appropriateness for use cases (e.g., use of ingredient combinations for perfumes/colognes versus shampoos versus hand soaps).

SUMMARY

In accordance with an embodiment of the present invention, a system for producing a formulation based on a prior distribution of a number of ingredients used in the formulation is provided. The system includes a memory device for storing program code and at least one processor device operatively coupled to the memory device. The at least one processor device is configured to execute program code stored on the memory device to group a set of energy functions based on a number of ingredients used in a formulation, generate a probability distribution using the set of energy functions, obtain at least one sample of the formulation by sampling from the probability distribution based on a previous sample, and trigger fabrication of the formulation in accordance with the at least one sample.

In accordance with another embodiment of the present invention, a computer-implemented method for producing a formulation based on a prior distribution of a number of ingredients used in the formulation is provided. The method includes grouping a set of energy functions based on a number of ingredients used in a formulation, generating a probability distribution using the set of energy functions, obtaining at least one sample of the formulation by sampling from the probability distribution based on a previous sample, and triggering fabrication of the formulation in accordance with the at least one sample.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

The embodiments described herein can produce a formulation based on a prior distribution of a number of ingredients used in the formulation in a manner that increases efficiency. For example, efficiency of sampling performed by an artificial intelligence agent of a formulation production system (e.g., a fragrance formulation production system) can be increased by taking into account a prior distribution of the number of ingredients used in a formulation. Instead of sampling a formulation from scratch each time, the embodiments described herein enable formulation sampling (e.g., employing a Markov chain Monte Carlo (MCMC) method) from a probability distribution by changing a certain pair of composition ratios of ingredients based on a previous sample to enable the sampling of formulations meeting pre-defined sample conditions. Selecting appropriate compositions of ingredients for producing formulations, in accordance with the embodiments described herein, can reduce computational intensity and thus improve the ability of a processor device implementing the artificial intelligence agent to sample formations for production based on the set of ingredients (e.g., by decreasing resource consumption and/or processing time). Such improvements can particularly be realized where the set of total possible ingredients for generating the formulation is relatively large (e.g., in the thousands), as compared to the number of ingredients selected from the set of total possible ingredients for generating the formulation (e.g., in the tens).

Figure 1:
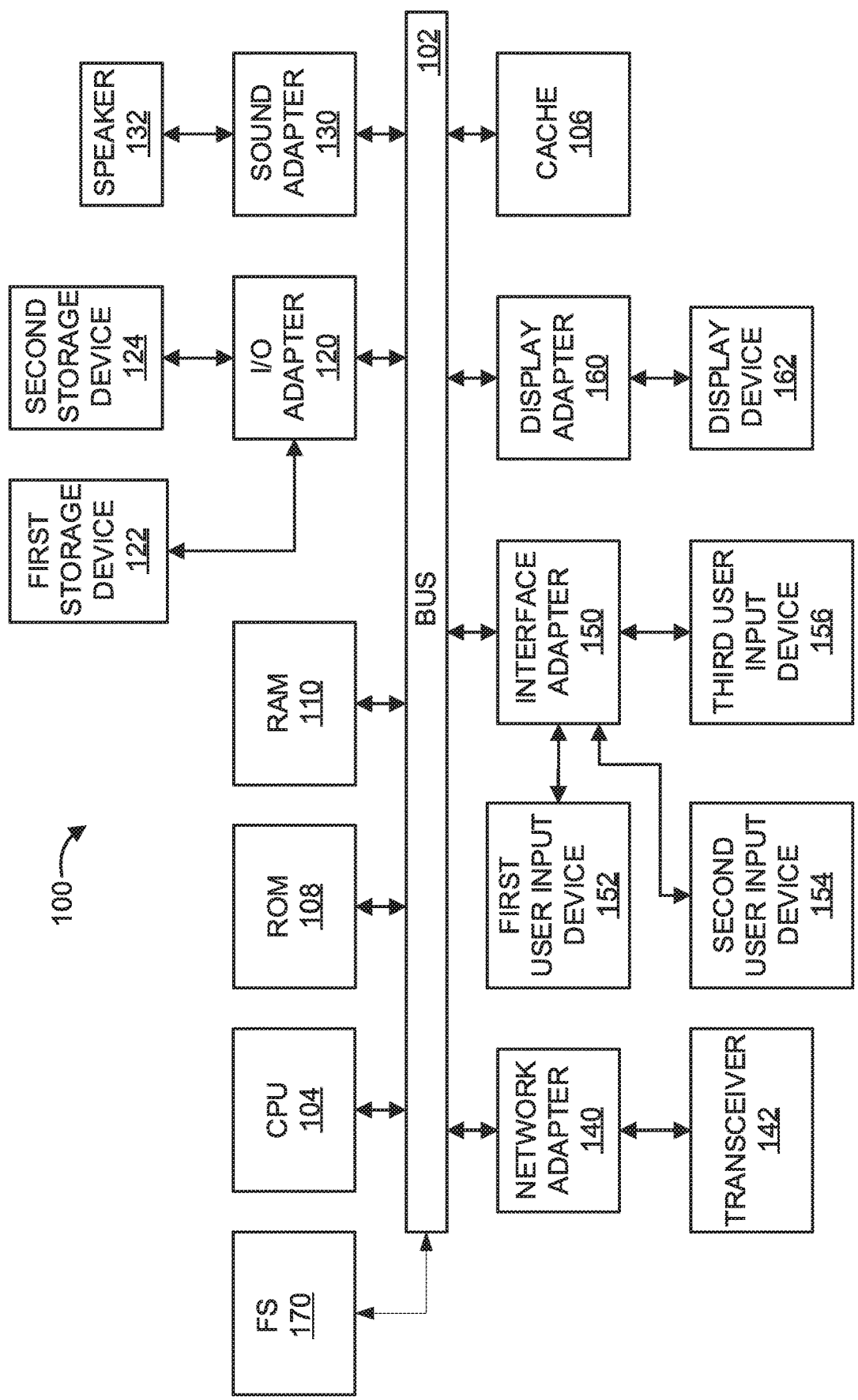
FIG. 1 is a block diagram of a processing system, in accordance with an embodiment of the present invention.

Referring now to the drawings in which like numerals represent the same or similar elements and initially to FIG. 1, an exemplary processing system 100 to which the present invention may be applied is shown in accordance with one embodiment. The processing system 100 includes at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160, are operatively coupled to the system bus 102.

A first storage device 122 and a second storage device 124 are operatively coupled to system bus 102 by the I/O adapter 120. The storage devices 122 and 124 can be any of a disk storage device (e.g., a magnetic or optical disk storage device), a solid state magnetic device, and so forth. The storage devices 122 and 124 can be the same type of storage device or different types of storage devices.

A speaker 132 is operatively coupled to system bus 102 by the sound adapter 130. A transceiver 142 is operatively coupled to system bus 102 by network adapter 140. A display device 162 is operatively coupled to system bus 102 by display adapter 160.

A first user input device 152, a second user input device 154, and a third user input device 156 are operatively coupled to system bus 102 by user interface adapter 150. The user input devices 152, 154, and 156 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present invention. The user input devices 152, 154, and 156 can be the same type of user input device or different types of user input devices. The user input devices 152, 154, and 156 are used to input and output information to and from system 100.

Formulation sampling (FS) component 170 may be operatively coupled to system bus 102. FS component 170 is configured to sample formulations within a formulation generation system as described in further detail below. FS component 170 can be implemented as a standalone special purpose hardware device, or may be implemented as software stored on a storage device. In the embodiment in which FS component 170 is software-implemented, although shown as a separate component of the computer system 100, FS component 170 can be stored on, e.g., the first storage device 122 and/or the second storage device 124. Alternatively, FS component 170 can be stored on a separate storage device (not shown).

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 100 are readily contemplated by one of ordinary skill in the art given the teachings of the present invention provided herein.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 2:
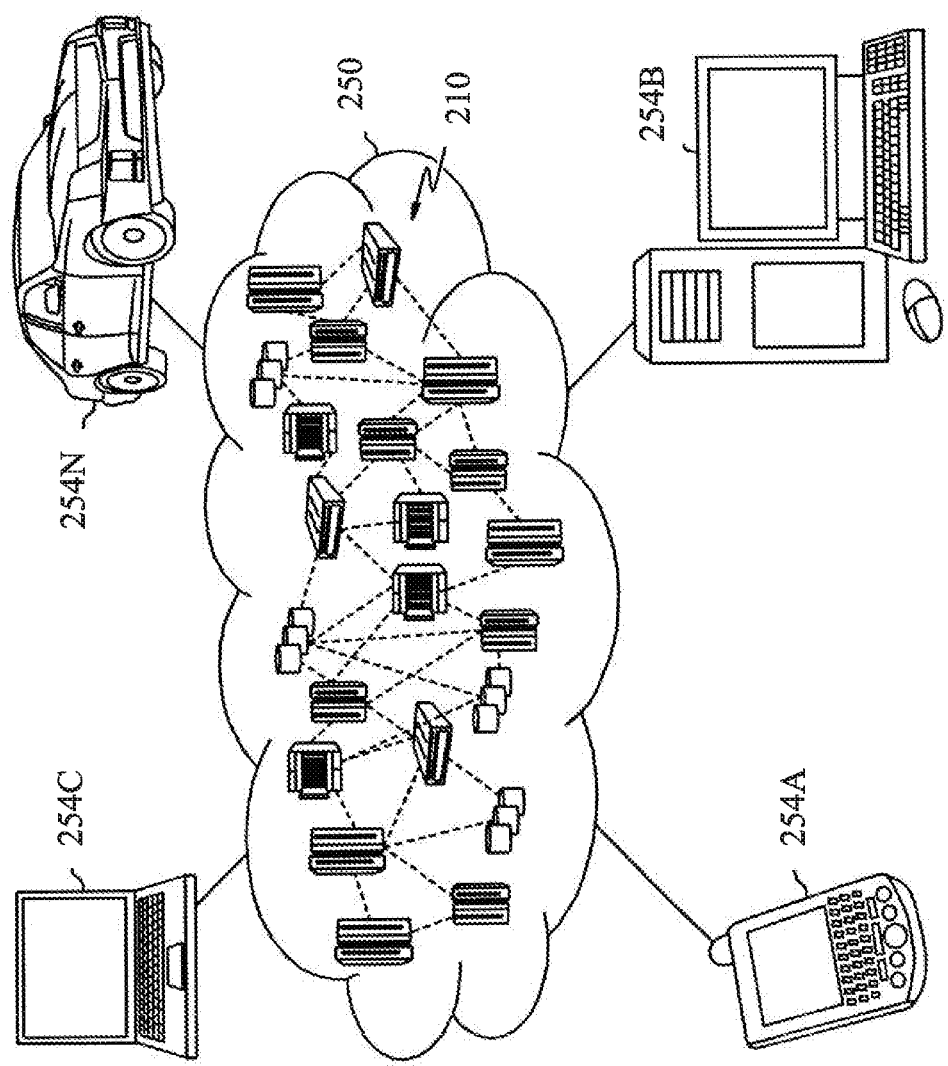
FIG. 2 is a block diagram of an illustrative cloud computing environment having one or more cloud computing nodes with which local computing devices used by cloud consumers communicate, in accordance with an embodiment of the present invention.

Referring now to FIG. 2, illustrative cloud computing environment 250 is depicted. As shown, cloud computing environment 250 includes one or more cloud computing nodes 210 with which local computing devices used by cloud consumers, such as, for example, personal digital assistant (PDA) or cellular telephone 254A, desktop computer 254B, laptop computer 254C, and/or automobile computer system 254N may communicate. Nodes 210 may communicate with one another. They may be grouped (not shown) physically or virtually, in one or more networks, such as Private, Community, Public, or Hybrid clouds as described hereinabove, or a combination thereof. This allows cloud computing environment 150 to offer infrastructure, platforms and/or software as services for which a cloud consumer does not need to maintain resources on a local computing device. It is understood that the types of computing devices 254A-N shown in FIG. 2 are intended to be illustrative only and that computing nodes 210 and cloud computing environment 250 can communicate with any type of computerized device over any type of network and/or network addressable connection (e.g., using a web browser).

Figure 3:
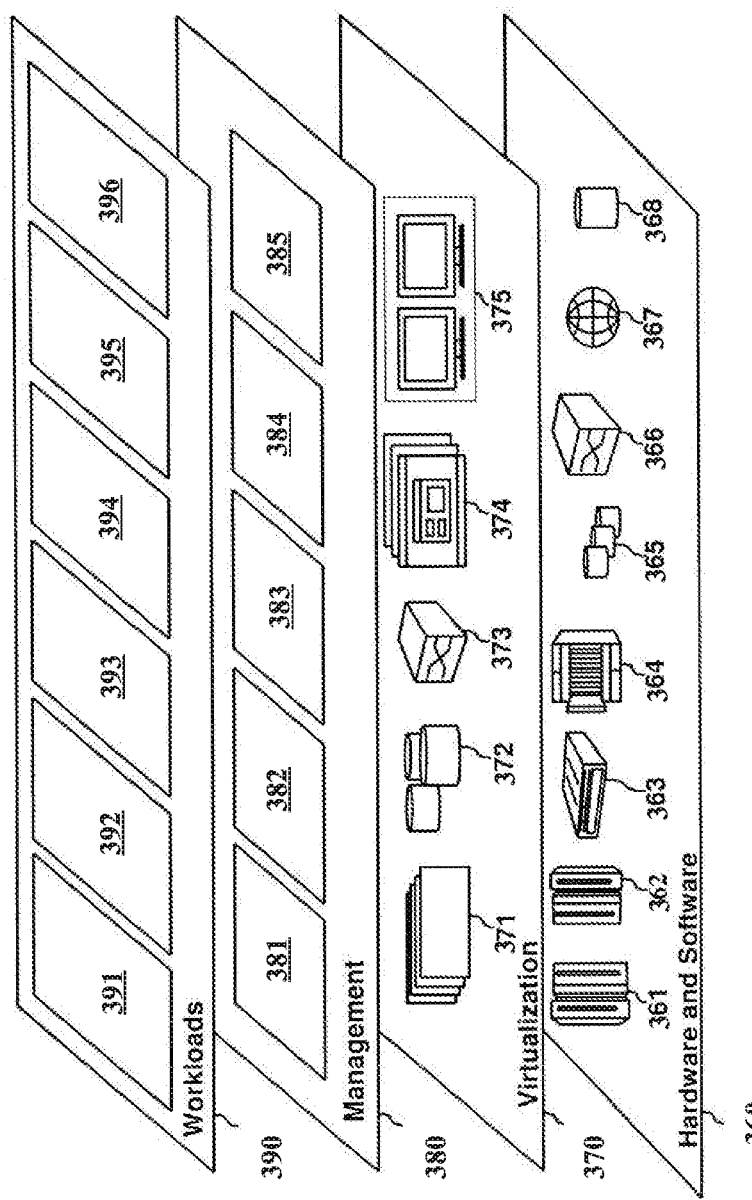
FIG. 3 is a block diagram of a set of functional abstraction layers provided by a cloud computing environment, in accordance with an embodiment of the present invention.

Referring now to FIG. 3, a set of functional abstraction layers provided by cloud computing environment 250 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 360 includes hardware and software components. Examples of hardware components include: mainframes 361; RISC (Reduced Instruction Set Computer) architecture based servers 362; servers 363; blade servers 364; storage devices 365; and networks and networking components 366. In some embodiments, software components include network application server software 367 and database software 368.

Virtualization layer 370 provides an abstraction layer from which the following examples of virtual entities may be provided: virtual servers 371; virtual storage 372; virtual networks 373, including virtual private networks; virtual applications and operating systems 374; and virtual clients 375.

In one example, management layer 380 may provide the functions described below. Resource provisioning 381 provides dynamic procurement of computing resources and other resources that are utilized to perform tasks within the cloud computing environment. Metering and Pricing 382 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 383 provides access to the cloud computing environment for consumers and system administrators. Service level management 384 provides cloud computing resource allocation and management such that required service levels are met. Service Level Agreement (SLA) planning and fulfillment 385 provide pre-arrangement for, and procurement of, cloud computing resources for which a future requirement is anticipated in accordance with an SLA.

Workloads layer 390 provides examples of functionality for which the cloud computing environment may be utilized. Examples of workloads and functions which may be provided from this layer include: mapping and navigation 391; software development and lifecycle management 392; virtual classroom education delivery 393; data analytics processing 394; transaction processing 395; and telematics data processing 396.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Figure 4:
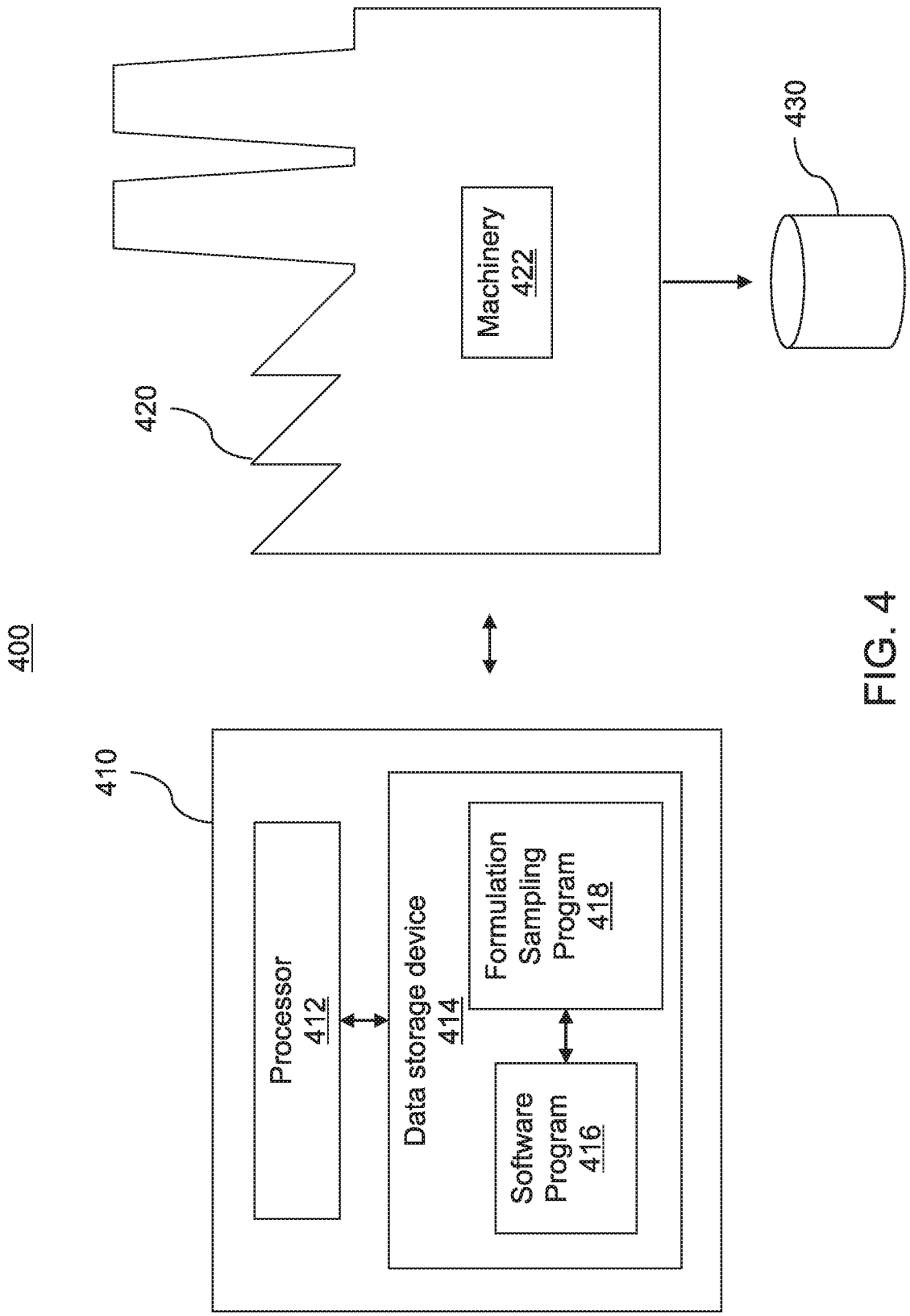
FIG. 4 is a block diagram of a system for producing a formulation based on a prior distribution of a number of ingredients used in the formulation, in accordance with an embodiment of the present invention.

With reference to FIG. 4, a diagram is provided illustrating an exemplary formulation production system 400. In one embodiment, the system 400 can produce fragrance formulations. However, any suitable formulations can be produced by the system 400 in accordance with the embodiments described herein.

As shown, the system 400 includes a processing device 410 and a fabrication center 420 (e.g., factory). The processing device 410 is configured to perform formulation sampling and generation based on compositions of ingredients, as will be described in further detail below with reference to FIGS. 5 and 6. Although the processing device 410 is shown external from the fabrication center 420, the processing device 410 can be located within the fabrication center 420. The fabrication center 420 can include machinery 422 configured to fabricate a product 430 determined based on results of the processing device 410. More specifically, the fabrication center 420 can include machinery 422 configured to fabricate the product 430 in response to the processing device 410 triggering fabrication of the formulation in accordance with the sampling, as will be described in further detail below with reference to FIGS. 5 and 6. For example, the product 430 can be a fragrance product (e.g., cologne or perfume) having compositions of ingredients having certain properties.

The processing device 410 may include a processor 412 and a data storage device 414 that is enabled to host and run a software program 416 and a formulation sampling program 418. The processing device 410 may be any type of computing device capable of running a program and accessing a network. Processing device 410 may also operate in a cloud computing service model, such as Software as a Service (SaaS), Platform as a Service (PaaS), or Infrastructure as a Service (IaaS). Processing device 410 may also be located in a cloud computing deployment model, such as a private cloud, community cloud, public cloud, or hybrid cloud.

Software program 416 may represent any program or suite of programs that call or communicate with formulation sampling program 418. For example, software program 416 can be a program or suite of software programs that call formulation sampling program 418 as a module for providing formulation sampling and generation functionality. In an alternate embodiment, software program 416 may be a database program that furnishes data to formulation sampling program 418.

Figure 5:
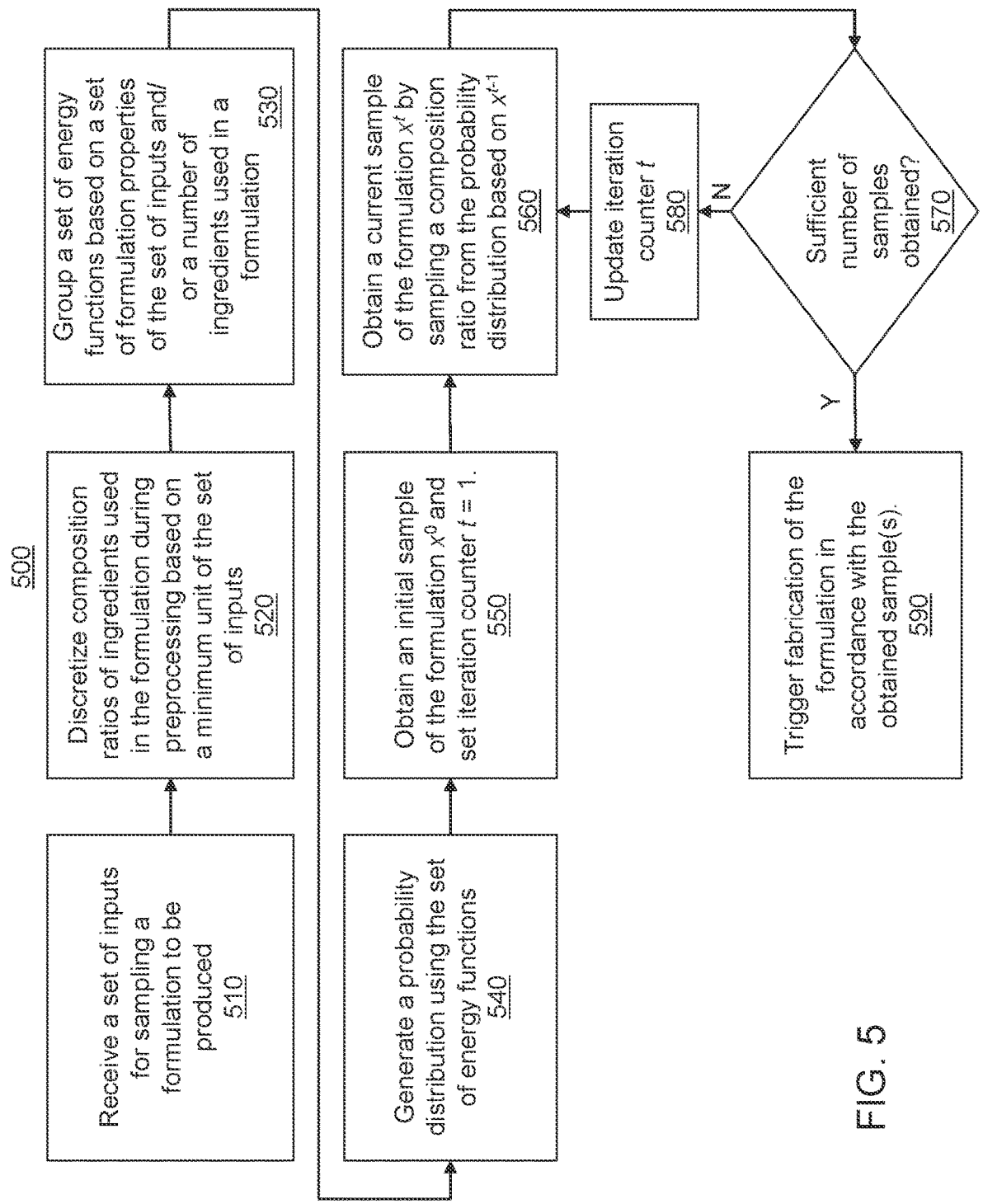
FIG. 5 is a block/flow diagram of a system/method for producing a formulation based on a prior distribution of a number of ingredients used in the formulation, in accordance with an embodiment of the present invention.

With reference to FIG. 5, a block/flow diagram is provided illustrating a system/method 500 for producing a formulation based on a prior distribution of a number of ingredients used in the formulation. Illustratively, the formulations produced by the system/method 500 can include fragrance formulations. However, system/method 500 can be used to produce any type of formulation in accordance with the embodiments described herein.

At block 510, a set of inputs is received for sampling a formulation to be produced. For example, for a formulation $x=\{x_0, \ldots, x_i, \ldots, x_N\}$ (where $x_i$ is the composition rate of ingredient i and is a non-negative integer ranging from 0 to M, and N is a maximum number of ingredients), the set of inputs can include a minimum unit 1/M for discretizing composition ratios (where M corresponds to sum of elements of a composition vector of the formulation x), and a set of formulation properties $y=\{y_0, \ldots, y_j, \ldots, y_L\}$. The formulation properties can relate to desired conditions and properties of the formulation, such as, e.g., a number of ingredients used in the formulation. For example, in the case where the formulation includes a fragrance formulation, the set of formulation properties can include a set of properties $y=\{y_a, y_f, y_c\}$, where $y_a$ represents aroma conditions, $y_f$ represents general conditions of fragrance formulations, and $y_c$ is a condition for a number of ingredients n used in the fragrance formulation. The condition for the number of ingredients n used in the fragrance formulation, $y_c$, can be received as a multinomial distribution.

At block 520, composition ratios of the ingredients used in the formulation can be discretized during preprocessing based on the minimum unit 1/M.

At block 530, a set of energy functions can be grouped based on the set of formulation properties. The set of energy functions at block 530 can be used to keep the samples sparse, which can more effectively handle scenarios where ratios are distributed among many ingredients, such that the number of ingredients used in the formulation, n, can be larger. This process can enable the computation of a probability distribution of the formulation, P(x|y), and to sample formulations based the conditions and the number of ingredients used in the formulation (e.g., using MCMC).

For example, in the case of fragrance formulations, a set of energy functions $E=\{E_a, E_f, E_c\}$ can be obtained, where $E_a$ refers to an aroma energy function that decreases when the formulation x meets $y_a$, $E_f$ refers to a formulation energy function that decreases when the formulation x meets $y_f$, and $E_c$ refers to a count energy function that decreases when the formulation x meets $y_c$.

In one embodiment, grouping the set of energy functions can include designing the energy function $E_c$ for the number of ingredients used in the at least one formulation, n, considering the number of formulations with the same number of ingredients. More specifically, a target distribution for the number of ingredients used in the at least one formulation n, $y_c(n)$, can be defined as $y_c(n)=Pr(f(x)=n)$, where f(x) is a function outputting the number of ingredients n used in the at least one formulation x. The energy function $E_c$ can then be designed as $E_c(x|y_c)=-\log(p(x|y_c))+D$, where D is an arbitrary constant and $$p(x' \mid y_c) = \exp(-E_c(x' \mid y_c)) \propto p(x, y_c) = \frac{y_c(f(x'))}{\sum_{x \in \mathcal{X}} \mathbb{I}(f(x) = f(x'))},$$

where $\mathbb{I}$ is an indicator function.

At block 540, a probability distribution is generated using the set of energy functions. Since the set of energy functions express properties or conditions of the formulation, incorporating the set of energy functions into the probability distribution can allow for the generation of formulations that take such properties or conditions into account. Illustratively, a probability distribution P(x|y) can be generated using the set of energy functions as follows:

$$P(x \mid y) = \frac{\exp\{-E_a(x \mid y_a) - E_f(x \mid y_f) - E_c(x \mid y_c)\}}{\sum_x \exp\{-E_a(x \mid y_a) - E_f(x \mid y_f) - E_c(x \mid y_c)\}}$$

The probability distribution generated at block 540 can be sampled to obtain a sample of the formulation corresponding to a current iteration. More specifically, at block 550, an initial sample of the formulation, $x^0$, can be obtained, and an iteration counter t is initialized to 1 and, at block 560, a current sample of the formulation, $x^t$, can be obtained by sampling from the probability distribution based on a previous sample $x^{(t-1)}$. Instead of sampling a formulation from scratch (which can increase computational resources used to generate and produce formulations), the formulation can be sampled by changing a pair of composition ratios of ingredients based on the previous sample. Further details regarding block 560 will now be described below with reference to FIG. 6.

At block 570, it is determined whether a sufficient number of samples have been obtained. If not, the iteration counter t is updated to t=t+1 at block 580, and another sample is obtained at block 560.

If a sufficient number of samples have been obtained, then system/method 500 can proceed to block 590 to trigger fabrication of the formulation in accordance with the obtained sample(s). For example, if the formulation is a fragrance formulation, a fragrance formulation can be bottled based on the compositions of ingredients that have the desired aroma properties in accordance with the sampling. The formulation can be fabricated in a cost effective manner and/or can be made with ingredients on hand, thereby increasing productivity.

Figure 6:
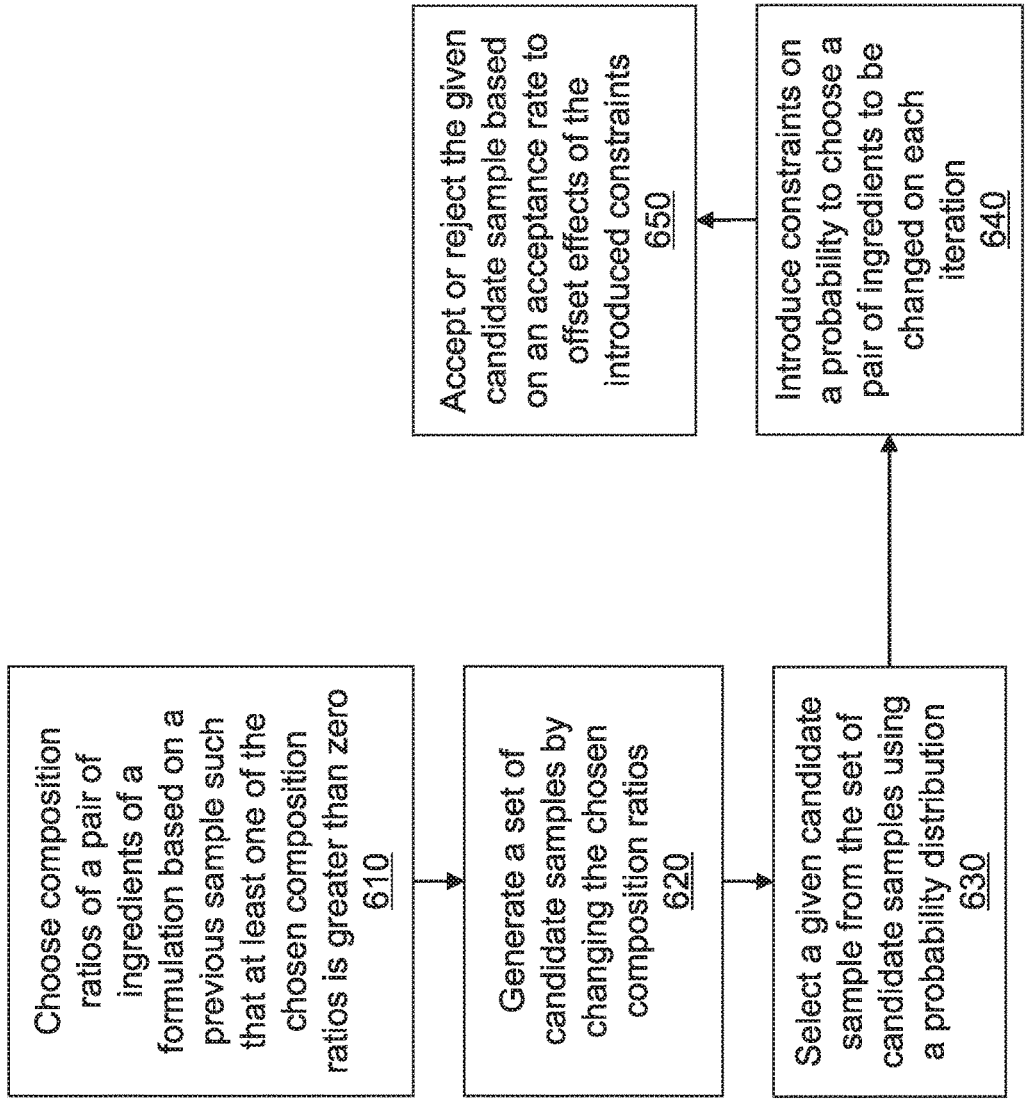
FIG. 6 is block/flow diagram of a system/method for sampling a formulation, in accordance with an embodiment of the present invention.

With reference to FIG. 6, a block/flow diagram is provided illustrating a system/method 600 for sampling a formulation based on a previous sample (e.g., such as in block 560 of FIG. 5).

At block 610, composition ratios of a pair of ingredients are chosen based on a previous sample such that at least one of the chosen composition ratios is greater than zero.

At block 620, a set of candidate samples can be generated by changing the chosen composition ratios.

At block 630, a given candidate sample is selected from the set of candidate samples using a probability distribution.

At block 640, constraints are introduced on a probability to choose a pair of ingredients to be changed on each iteration and, at block 650, the given candidate sample is accepted or rejected based on an acceptance rate (e.g., MCMC acceptance rate) to offset effects of the introduced constraints. The process can repeat until a sufficient number of samples have been accepted. The processes performed at blocks 640 and 650 allow for the efficient sampling of formulations. For example, sampling the same formulations many times can be avoided, and there is a lack of bias in the results of the sampling.

As an example of an implementation of blocks 610-650, ingredients i and j can be chosen to be changed at random (where i≠j). To generate a given candidate sample x', candidate sample ingredients $x_i'$ and $x_j'$ can be selected and combined with the previous sample $x^{(t-1)}$, excluding the ingredients $x_i^{(t-1)}$ and $x_j^{(t-1)}$ of the previous sample $x^{(t-1)}$, into the given candidate sample x'.

Let Q(x, x') be defined as the probability to select x' as a candidate from x, $a_{ij}(x)$ be the probability to choose the pair of ingredients i and j to be changed, and r(x, x') be the transition probability x→x'. The acceptance rate can be defined as, e.g., min(1, r) where $$r = \frac{P(x')Q(x', x)}{P(x)Q(x, x')}.$$

Q(x, x') doesn't necessarily equal Q(x', x), since Q(x, x')∝$\alpha_{ij}(x)$, Q(x', x)∝$\alpha_{ij}(x')$.

Where the sampling method uses MCMC, an initial state $x^{(0)}$ from an initial probability distribution $P_0$ can converge to probability distribution P(x) as t→∞. The probability distribution of step t, $P_t(x)$, can evolve over time as follows: $P_{t+1}(x')=\Sigma_x P_t(x)\pi(x, x')$. If P(x) satisfies $P(x')=E_x P(x)\pi(x, x')$ for any x, then $P_t(x)$ is a stationary distribution (e.g., an invariant probability distribution) if $P_t(x)$ converges to the distribution of P(x). A sufficient condition for a stationary distribution is the detailed balance condition, which provides that any x and x' satisfy P(x)π(x, x')=P(x')π(x', x). The embodiments described herein above with reference to FIGS. 5 and 6 can satisfy the detailed balance condition in the case of introducing constraints on the probability to choose a pair of ingredients to be changed on each iteration.

A composition x, as described above with reference to FIGS. 5 and 6, can be viewed as an allocation of M balls into N bins, where each ball corresponds to a minimum unit for discretizing the composition ratio (1/M), and each bin corresponds to a usable ingredient (e.g., a dimension of the composition vectors x). Accordingly, the number of balls in a given bin corresponds to a composition ratio allocated to the corresponding ingredient.

Assume that $x^{(t-1)}=\{x_1, x_2, \ldots x_N\}$, where there are 3 balls allocated to $x_1$ and 2 balls allocated to $x_3$ (the rest of the "bins" are empty). To update to x(t) in this example, it is assumed that $x_1$ and $x_2$ are chosen as a result of choosing two variables to be changed at random. The number of combinations of $x'_1$ and $x'_2$ corresponding to a given candidate sample x' in this example is 4. More specifically, 3 balls in $x'_1$ and 0 balls in $x'_2$ (the number of bins with balls in x', n', equals n), 2 balls in $x'_1$ and 1 ball in X'2 (n'=n+1), 1 ball in $x'_1$ and 2 balls in $x'_2$(n'=n+1), and 0 balls in $x'_1$ and 3 balls in $x'_2$ (n'=n). For the sake of comparison, if $x_1$ and $x_3$ were chosen instead of $x_1$ and $x_2$, the number of combinations of $x'_1$ and $x'_3$ would be 6. More specifically, 5 balls in $x'_1$ and 0 balls in $x'_3$ (n'=n−1), 4 balls in $x'_1$ and 1 ball in $x'_3$ (n'=n), 3 balls in $x'_1$ and 2 balls in $x'_3$(n'=n), 2 balls in $x'_1$ and 3 balls in $x'_3$ (n'=n), 1 ball in $x'_1$ and 4 balls in $x'_3$ (n'=n), and 0 balls in $x'_1$ and 5 balls in $x'_2$ (n'=n−1). As another example, if $x_2$ and $x_4$ were chosen instead of $x_1$ and $x_2$, the number of combinations of $x'_2$ and $x'_4$ would be 1 (n'=n).

The conditional distribution p(x|y) can be calculated for each combination of x' and x'2. Both $x'_1$ and $x'_2$ can be chosen and combined with the rest of $x^{(t-1)}$ into x'. Then, x' can be accepted or rejected as x(t) based on the acceptance rate (e.g., MCMC acceptance rate).

More generally, for M balls, N bins and n ones of the N bins with balls, the number of possible combinations can be represented as the product of (1) the number of combinations to choose n bins from N bins and (2) the number of combinations that put a ball in each of the chosen n bins and choose bins allocating the remaining (M−n) balls from the n bins, or $$\binom{N}{n}\binom{M-1}{M-n}.$$

In the above example of 5 balls and 50 bins, the following table illustrates the relationship between the number of bins with balls n and the number of combinations (1≤n≤5 since there are 5 balls):

TABLE 1

| n | 1 | 2 | 3 | 4 | 5 |
|---|---|---|---|---|---|
| # of combinations | 50 | 4,900 | 117,600 | 921,200 | 2,118,760 |

As can be seen, there can be an enormous number of combinations as n increases. The samples can be kept sparse by correction using the number of combinations as follows:

$$p(x' \mid y_c) =$$
$$\exp(-E_c(x' \mid y_c)) \propto p(x, y_c) = \frac{y_c(f(x'))}{\sum_{x \in \mathcal{X}} \mathbb{1}(f(x)=f(x'))} = \frac{y_c(n')}{\left\{\binom{N}{n'}\binom{M-1}{M-n'}\right\}}$$

When we choose a pair of bins to be changed where at least one of the composition ratios is greater than 0, the effect of this constraint can be offset by adjusting the acceptance rate using $\alpha_{ij}(x)$, the probability to choose a pair of bins to be changed. When x is sparse and a pair of empty bins (e.g., $x_2$ and $x_4$) are chosen at random, we often do not update x, resulting in poor sampling efficiency. When we choose a pair of bins i, j to be changed where at least one of the component ratios is greater than 0, $\alpha_{ij}(x)$ depends on n. In this case, $\alpha_{ij}(x)$ is the product of 1/n (the probability to choose $x_i$>0) and 1/(N−1) (the probability to choose $x_j$ except $x_i$). When $x_j$ is also greater than 0, $\alpha_{ij}(x)$ is 2/(n(N−1)). When $\alpha_{ij}(x)$ and $\alpha_{ij}(x')$ are not equal (as in some cases), we have to use the acceptance rate min(1, r) where $$r = \frac{P(x'|y)Q(x',x)}{P(x|y)Q(x,x')}.$$

For example, if $$n' = n, \text{ then } \alpha_{ij}(x) = \alpha_{ij}(x') = 2\frac{1}{n}\frac{1}{N-1} \text{ or } \frac{1}{n}\frac{1}{N-1}. \text{ If } n' = n-1,$$

$$\text{then } \alpha_{ij}(x) = 2\frac{1}{n}\frac{1}{N-1}, \alpha_{ij}(x') = \frac{1}{n-1}\frac{1}{N-1}. \text{ If } n' = n+1,$$

$$\text{then } \alpha_{ij}(x) = \frac{1}{n}\frac{1}{N-1}, \alpha_{ij}(x') = 2\frac{1}{n+1}\frac{1}{N-1}.$$

Figure 7:
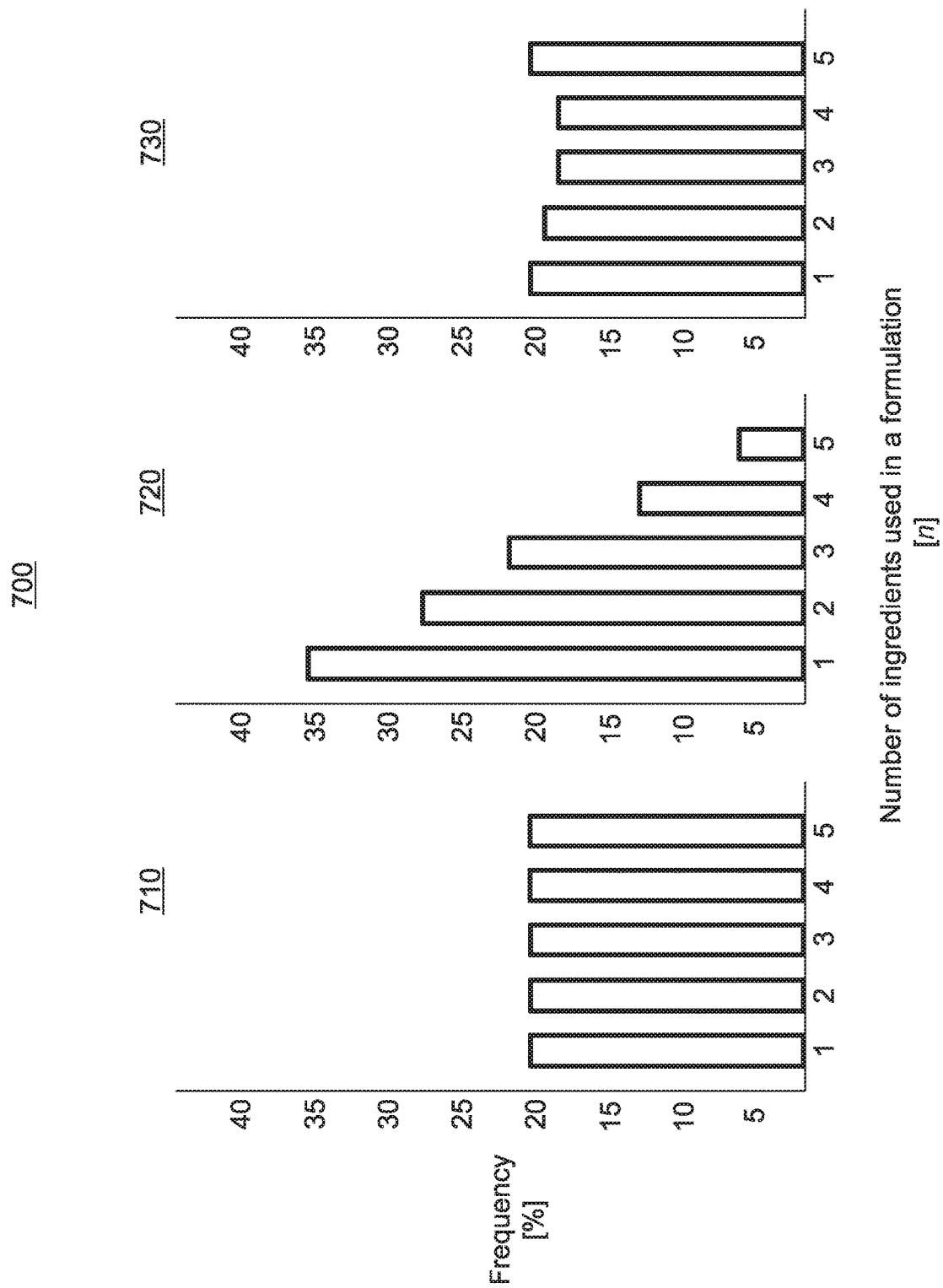
FIG. 7 is a diagram of experimental results, in accordance with an embodiment of the present invention.

With reference to FIG. 7, a diagram 700 is provided illustrating a plurality of histograms 710 through 730 corresponding to a first example. In this example, the number of usable ingredients N (e.g., the dimension of the composition vector x) is 50, the sum of elements of the discretized composition vector x is 5 ($\Sigma_i x_1 = M = 5$), the number of samples is 30,000, and the target distribution $y_c(n)$ is a uniform distribution, where n refers to the number of ingredients used in a formulation.

The abscissa of each histogram 710-730 corresponds to the number of ingredients used in a formulation (n), and the ordinate of each histogram corresponds to a corresponding frequency (%). More specifically, histogram 710 shows the target distribution $y_c(n)$, histogram 720 shows the histogram of n of samples in the case of an acceptance rate equal to 1, and histogram 730 shows the histogram of n samples in the case of an acceptance rate equal to min $$\left(1, \frac{\alpha_{ij}(x')}{\alpha_{ij}(x)}\right).$$

Figure 8:
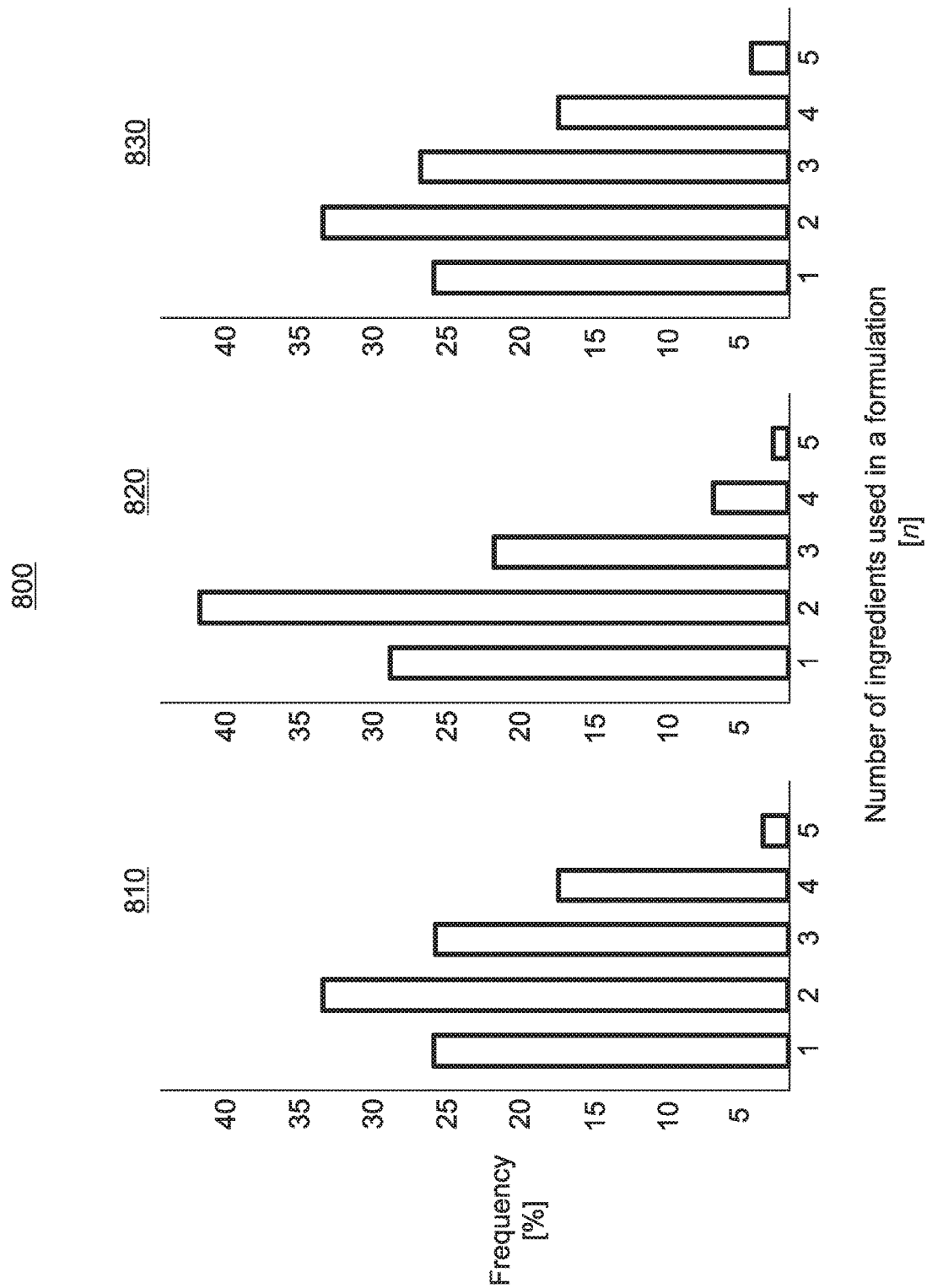
FIG. 8 is a diagram of experimental results, in accordance with another embodiment of the present invention.

With reference to FIG. 8, a diagram 800 is provided illustrating a plurality of histograms 810 through 830 corresponding to a second example. In this example, the number of usable ingredients N (e.g., the dimension of the composition vector x) is 50, the sum of elements of the discretized composition vector x is 5 ($\tau_i x_i = M = 5$), the number of samples is 30,000, and the target distribution $y_c(n)$ is a unimodal distribution, where n refers to the number of ingredients used in a formulation.

Similar to the histograms 710-730 of FIG. 6, the abscissa of each histogram 810-830 corresponds to the number of ingredients used in a formulation (n), and the ordinate of each histogram corresponds to a corresponding frequency (%). More specifically, histogram 810 shows the target distribution $y_c(n)$, histogram 720 shows the histogram of n of samples in the case of an acceptance rate equal to 1, and histogram 830 shows the histogram of n samples in the case of an acceptance rate equal to min $$\left(1, \frac{\alpha_{ij}(x')}{\alpha_{ij}(x)}\right).$$

Having described preferred embodiments of systems and methods of producing a formulation based on a prior distribution of a number of ingredients used in the formulation (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed:

1. A system for producing a formulation based on a prior distribution of a number of ingredients used in the formulation, comprising:
   a memory device for storing program code; and
   at least one processor device operatively coupled to the memory device and configured to execute program code stored on the memory device to:
   group a set of energy functions based on a number of ingredients used in a formulation;
   generate a probability distribution using the set of energy functions;
   obtain at least one sample of the formulation by sampling from the probability distribution based on a previous sample; and
   trigger fabrication of the formulation in accordance with the at least one sample.

2. The system of claim 1, wherein the at least one processor device is further configured to execute program code stored on the memory device to receive a set of inputs for sampling the formulation, and discretize composition ratios of the ingredients used in the formulation based on the set of inputs.

3. The system of claim 1, wherein the at least one processor device is further configured to receive the condition corresponding to the number of ingredients used in the formulation as a multinomial distribution.

4. The system of claim 1, wherein the at least one processor device is further configured to obtain the at least one sample by:
   choosing composition ratios of a pair of ingredients of the formulation based on the previous sample such that at least one of the chosen composition ratios is greater than zero;
   generating a set of candidate samples by changing the chosen composition ratios;
   selecting a given sample from the set of candidate samples using the probability distribution; and
   accepting the given sample based on an acceptance rate to offset constraint effects.

5. The system of claim 4, wherein the at least one processor device is further configured to obtain the at least one sample by introducing constraints on a probability to choose a pair of ingredients to be changed on each iteration.

6. The system of claim 1, wherein the formulation includes a fragrance formulation.

7. The system of claim 1, further comprising a fabrication center configured to fabricate the formulation in accordance with the at least one sample in response to the triggering.

8. A computer-implemented method for producing a formulation based on a prior distribution of a number of ingredients used in the formulation, comprising:
   grouping a set of energy functions based on a number of ingredients used in a formulation;
   generating a probability distribution using the set of energy functions;
   obtaining at least one sample of the formulation by sampling from the probability distribution based on a previous sample; and triggering fabrication of the formulation in accordance with the at least one sample.

9. The method of claim 8, further comprising receiving a set of inputs for sampling the formulation, and discretizing composition ratios of the ingredients used in the formulation based on the set of inputs.

10. The method of claim 8, wherein the condition corresponding to the number of ingredients used in the formulation is received as a multinomial distribution.

11. The method of claim 8, wherein obtaining the at least one sample further includes:
choosing composition ratios of a pair of ingredients of the formulation based on the previous sample such that at least one of the chosen composition ratios is greater than zero;
generating a set of candidate samples by changing the chosen composition ratios;
selecting a given sample from the set of candidate samples using the probability distribution; and
accepting the given sample based on an acceptance rate to offset constraint effects.

12. The method of claim 11, wherein the obtaining the at least one sample further includes introducing constraints on a probability to choose a pair of ingredients to be changed on each iteration.

13. The method of claim 8, wherein the formulation includes a fragrance formulation.

14. The method of claim 8, further comprising fabricating the formulation in accordance with the at least one sample in response to the triggering.

15. A computer program product comprising a non-transitory computer readable storage medium having program instructions embodied therewith, the program instructions executable by a computer to cause the computer to perform a method for producing a formulation based on a prior distribution of a number of ingredients used in the formulation, the method performed by the computer comprising:
grouping a set of energy functions based on a number of ingredients used in a formulation;
generating a probability distribution using the set of energy functions;
obtaining at least one sample of the formulation by sampling from the probability distribution based on a previous sample; acid
triggering fabrication of the formulation in accordance with the at least one sample.

16. The computer program product of claim 15, wherein the method further comprises receiving a set of inputs for sampling the formulation, and discretizing composition ratios of the ingredients used in the formulation based on the set of inputs.

17. The computer program product of claim 15, wherein the condition corresponding to the number of ingredients used in the formulation is received as a multinomial distribution.

18. The computer program product of claim 15, wherein obtaining the at least one sample further includes:
choosing composition ratios of a pair of ingredients of the formulation based on the previous sample such that at least one of the chosen composition ratios is greater than zero;
generating a set of candidate samples by changing the chosen composition ratios;
selecting a given sample from the set of candidate samples using the probability distribution; and
accepting the given sample based on an acceptance rate to offset constraint effects.

19. The computer program product of claim 18, wherein the obtaining the at least one sample further includes introducing constraints on a probability to choose a pair of ingredients to be changed on each iteration.

20. The computer program product of claim 15, wherein the method further comprises fabricating the formulation in accordance with the at least one sample in response to the triggering.

* * * * *